(12) United States Patent
Mann et al.

(10) Patent No.: US 6,458,102 B1
(45) Date of Patent: Oct. 1, 2002

(54) EXTERNAL GAS POWERED PROGRAMMABLE INFUSION DEVICE

(75) Inventors: Alfred E. Mann, Beverly Hills; H. Lee Renger, Calabasas; Clyde Nason, Valencia; Hiwa Nezhadian, Simi Valley, all of CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 09/578,566

(22) Filed: May 25, 2000

Related U.S. Application Data (60) Provisional application No. 60/136,733, filed on May 28, 1999, and provisional application No. 60/138,183, filed on Jun. 8, 1999.

(51) Int. Cl.[7] .............................................. A61M 37/00
(52) U.S. Cl. ...................... 604/131; 604/140; 604/141; 604/145; 222/399
(58) Field of Search ................................ 604/131, 132, 604/140, 141, 143, 145, 153; 222/105, 95, 399, 386.5; 128/DIG. 12

(56) References Cited

U.S. PATENT DOCUMENTS

| | | | | |
|---|---|---|---|---|
| 3,023,750 A | * | 3/1962 | Baron ......................... | 604/141 |
| 4,886,499 A | * | 12/1989 | Cirelli et al. ................. | 604/131 |
| 4,969,874 A | * | 11/1990 | Michel et al. ................ | 604/140 |
| 5,041,094 A | * | 8/1991 | Perego et al. ................ | 604/131 |
| 5,090,963 A | * | 2/1992 | Gross et al. .................. | 604/132 |
| 5,135,499 A | | 8/1992 | Tafani et al. .................. | 604/141 |
| 5,242,406 A | | 9/1993 | Gross et al. .................. | 604/132 |
| 5,368,571 A | * | 11/1994 | Horres, Jr. .................... | 604/131 |
| 5,399,166 A | * | 3/1995 | Laing ........................... | 604/131 |
| 5,553,741 A | * | 9/1996 | Sancoff et al. ................ | 604/145 |
| 5,567,287 A | | 10/1996 | Joshi et al. ................... | 204/265 |
| 5,700,245 A | * | 12/1997 | Sancoff et al. ................ | 604/145 |
| 5,704,520 A | * | 1/1998 | Gross ........................... | 604/141 |
| 5,785,688 A | * | 7/1998 | Joshi et al. ................... | 604/141 |
| 5,891,097 A | | 4/1999 | Saito et al. ................... | 604/141 |

FOREIGN PATENT DOCUMENTS

| | | | | |
|---|---|---|---|---|
| EP | 0481601 | | 9/1991 | ........... A61M/5/155 |
| WO | 9532013 | | 11/1995 | ........... A61M/5/168 |

* cited by examiner

*Primary Examiner*—Teresa Walberg
*Assistant Examiner*—Fadi H. Dahbour
(74) *Attorney, Agent, or Firm*—Medtronic MiniMed, Inc.

(57) ABSTRACT

An external infusion device system for infusing a fluid into a patient, the system including a reusable infusion device housing, a gas power source and disposable reservoir. The disposable reservoir is insertable into the reusable infusion device housing to infuse the fluid into the patient. The gas power source is for generating a gas to expel the fluid from the fluid reservoir. The disposable reservoir includes a reservoir housing, a fluid reservoir, an outlet, a gas power source, an expansion chamber and a regulating valve assembly. The fluid reservoir is within the reservoir housing for containing the fluid to be infused into the patient. The outlet is in the reservoir housing and provides a path through which the fluid is expelled to be infused into the patient. The expansion chamber is disposed between the gas power source and the fluid reservoir to receive the gas from the gas power source. The expansion member expands into the fluid reservoir to expel the fluid from the fluid reservoir. The regulating valve assembly is disposed between the fluid reservoir and the outlet to set a predetermined threshold pressure that must be exceeded to permit fluid to be expelled from the fluid reservoir through the outlet. In preferred embodiments, the fluid to be infused is a medication. Also, the regulating valve assembly sets the predetermined threshold pressure at greater than 1.05 atmospheres.

22 Claims, 9 Drawing Sheets

EXTERNAL GAS POWERED PROGRAMMABLE INFUSION DEVICE

This application claims benefit of Provisional Applications 60/136,733 filed May 28, 1999 and 60/138,183 filed Jun. 8, 1999.

FIELD OF THE INVENTION

This invention relates to external, gas powered programmable infusion devices, and in particular embodiments, to an external gas powered programmable infusion device that utilizes a disposable medication cartridge with gas power source.

BACKGROUND OF THE INVENTION

Insulin must be provided to people with Type I, and many with Type II diabetes. Traditionally, since it cannot be taken orally, insulin has been injected with a syringe. More recently, use of external infusion pump therapy has been increasing, especially for delivering insulin for diabetics using devices worn on a belt, in a pocket, or the like, with the insulin delivered via a catheter with a percutaneous needle or cannula placed in the subcutaneous tissue. For example, as of 1995, less than 5% of Type I diabetics in the United States were using pump therapy. Currently, of the over 900,000 Type I diabetics in the U.S., about 7% use insulin pump therapy, and the percentage is now growing at an absolute rate of over 2% each year. Moreover, the number of Type I diabetics is growing at 3% or more per year. In addition, growing numbers of insulin using Type II diabetics are also using external insulin infusion pumps. Physicians have recognized that continuous infusion provides greater control of a diabetic's condition, and are also increasingly prescribing it for patients. In addition, medication pump therapy is becoming more important for the treatment and control of other medical conditions, such as pulmonary hypertension, HIV and cancer. Although offering control, pump therapy can suffer from several complications that make use of traditional external infusion pumps less desirable for the user.

For instance, one drawback is that traditional external pumps for profiled delivery of insulin and other drugs that require accurate titration are generally complex and expensive. Regarding costs, traditional external insulin pumps for treating Type 1 diabetes typically cost about $5,000 and the disposables cost about $800 to $1,200 per year. Generally, Type 2 diabetics often spend $3–$8 per day just for an oral medication rather than insulin. Thus, managed care providers are generally resistant to spending $5,000 for a pump, especially for a Type 2 diabetic, but seem less concerned about reimbursing for disposables or for the costly drugs.

Traditional external pumps are very sophisticated, with many safety features and checks. However, for some applications, such as for a Type 2 diabetic, a simpler and less expensive non-programmable pump system would often suffice. Conversely, programmability may still be desired or necessary to provide tighter control and flexibility. In addition, a programmable pump provides greater flexibility to use the external pump over a wider range of treatments and for a greater variety of medications.

SUMMARY OF THE DISCLOSURE

It is an object of an embodiment of the present invention to provide an integrated diabetes management system, which obviates for practical purposes, the above-mentioned limitations.

According to an embodiment of the invention, an external infusion device system for infusing a fluid into a patient, the system includes a reusable infusion device housing, a gas power source and disposable reservoir. The gas power source is for generating a gas to expel the fluid from the fluid reservoir. The disposable reservoir is insertable into the reusable infusion device housing to infuse the fluid into the patient. The disposable reservoir includes a reservoir housing, a fluid reservoir, an outlet, an expansion chamber and a regulating valve assembly. The fluid reservoir is within the reservoir housing for containing the fluid to be infused into the patient. The outlet is in the reservoir housing and provides a path through which the fluid is expelled to be infused into the patient. The expansion chamber is disposed between the gas power source and the fluid reservoir to receive the gas from the gas power source. The expansion member expands into the fluid reservoir to expel the fluid from the fluid reservoir. The regulating valve assembly is disposed between the fluid reservoir and the outlet to set a predetermined threshold pressure that must be exceeded to permit fluid to be expelled from the fluid reservoir through the outlet. In preferred embodiments, the fluid to be infused is a medication. Also, the regulating valve assembly sets the predetermined threshold pressure at a pressure somewhat above standard atmospheric pressure, such as greater than 1.05 atmospheres.

In particular embodiments, the gas power source utilizes electrolysis to generate the gas. In other embodiments, the gas power source includes a housing, and the gas power source uses the housing of the gas power source as an electrode. Also, the disposable reservoir can include a pressure sensor coupled to the gas power source to determine a pressure in the expansion chamber to detect an occlusion. In preferred embodiments, the disposable reservoir has a circular cross-section, while in other embodiments, the disposable reservoir has an oval cross-section. Preferably, the expansion chamber is formed as a sack, and in some embodiments the sack has a circular cross-section. In still further embodiments, the regulating valve assembly is compressed prior to use to set the predetermined threshold pressure. In particular embodiments, the gas power source is contained in the disposable reservoir. In other embodiments, the gas power source is contained in the device housing and engages with the disposable reservoir.

Other features and advantages of the invention will become apparent from the following detailed description, taken in conjunction with the accompanying drawings, which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 1b is an enlarged cross-sectional diagram of the regulating valve shown in FIG. 1a.

FIG. 4a is a front plan view of an infusion device in accordance with an embodiment of the present invention that utilizes the disposable reservoir shown in FIG. 1a.

FIG. 4b is an end plan view of the infusion device shown in FIG. 4a.

FIG. 5b is a partial cross-sectional view of the electrical contacts in the infusion device for contacting with the electrical contacts of the disposable reservoir shown in FIG. 5a.

FIG. 6 is a front plan view of an infusion device in accordance with an embodiment of the present invention for use with the disposable reservoir shown in FIG. 5a.

FIG. 7b shows a fluid cell for use with the electrodes of the disposable reservoir shown in FIG. 5a.

FIG. 8b shows a side cross-sectional view of the disposable reservoir shown in FIG. 8a.

DETAILED DESCRIPTION OF THE PREFERRED EMBODIMENTS

As shown in the drawings for purposes of illustration, the invention is embodied in an infusion device for infusion of a liquid, such as medication, chemicals, enzymes, antigens, hormones, vitamins or the like, into a body of a user. In preferred embodiments of the present invention, the infusion device uses a disposable reservoir containing a gas power source. However, it will be recognized that further embodiments of the invention may be used with a gas power source that is resident in the infusion device rather than the disposable reservoir. Particular embodiments are directed towards the use in humans; however, in alternative embodiments, the infusion devices may be used in animals. Preferred embodiments may utilize features that are similar to those found on other external programmable infusion devices, such as can be found in U.S. patent application Ser. No. 60/096,994 filed Aug. 18, 1998 (published as PCT application WO 00/10628) and is entitled "INFUSION DEVICE WITH REMOTE PROGRAMMING, CARBOHYDRATE CALCULATOR AND/OR VIBRATION ALARM CAPABILITIES," which is herein incorporated by reference.

FIGS. 1a–4b illustrate an infusion device 100 that utilizes a disposable reservoir 102 inserted into a reservoir chamber 40. FIG. 4a shows the infusion device 100 and in dotted lines how the disposable reservoir 102 (or cartridge) fits into the reservoir chamber 40. When the disposable reservoir 102 is inserted into the reservoir chamber 40, it can be locked in place by a variety of methods, such as friction, tabs, threads, snap fits, or the like. One version, shown in FIG. 4b, utilizes a slide lock 69 that includes a slot 106 formed by fingers 69' that surround a neck 20 of the disposable cartridge 102 to secure the disposable reservoir in the reservoir chamber 40 of the infusion device 100. In operation, the slide lock 69 is pushed across the end of the infusion device 100 to slide the fingers 69' around the neck 20 of the disposable reservoir 102. Also shown in FIG. 4a are a display 43 and control switches 44, 45, 46 and 47 to program the infusion device 100. For instance, the keys 44–47 and display 43 may be used to program the electrical current to be applied across the gas power source 3, such as an electrolysis cell or the like, to generate the gas that expands a reservoir sack 11 in the disposable cartridge 102 to push the medication, or the like, in a medication reservoir 4 out through an outlet 16 and through the regulating valve assembly 15 at the end of the disposable reservoir 102.

Figure 1A:
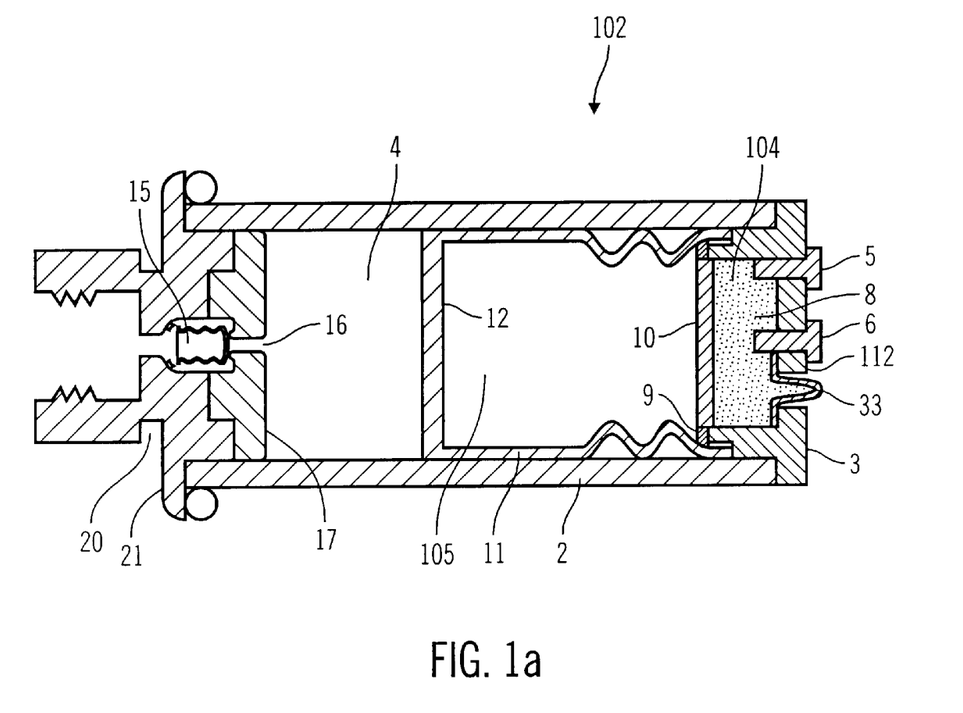
FIG. 1a is a cross-sectional view of a disposable reservoir containing a gas power source in accordance with a first embodiment of the present invention.
Figure 1B:
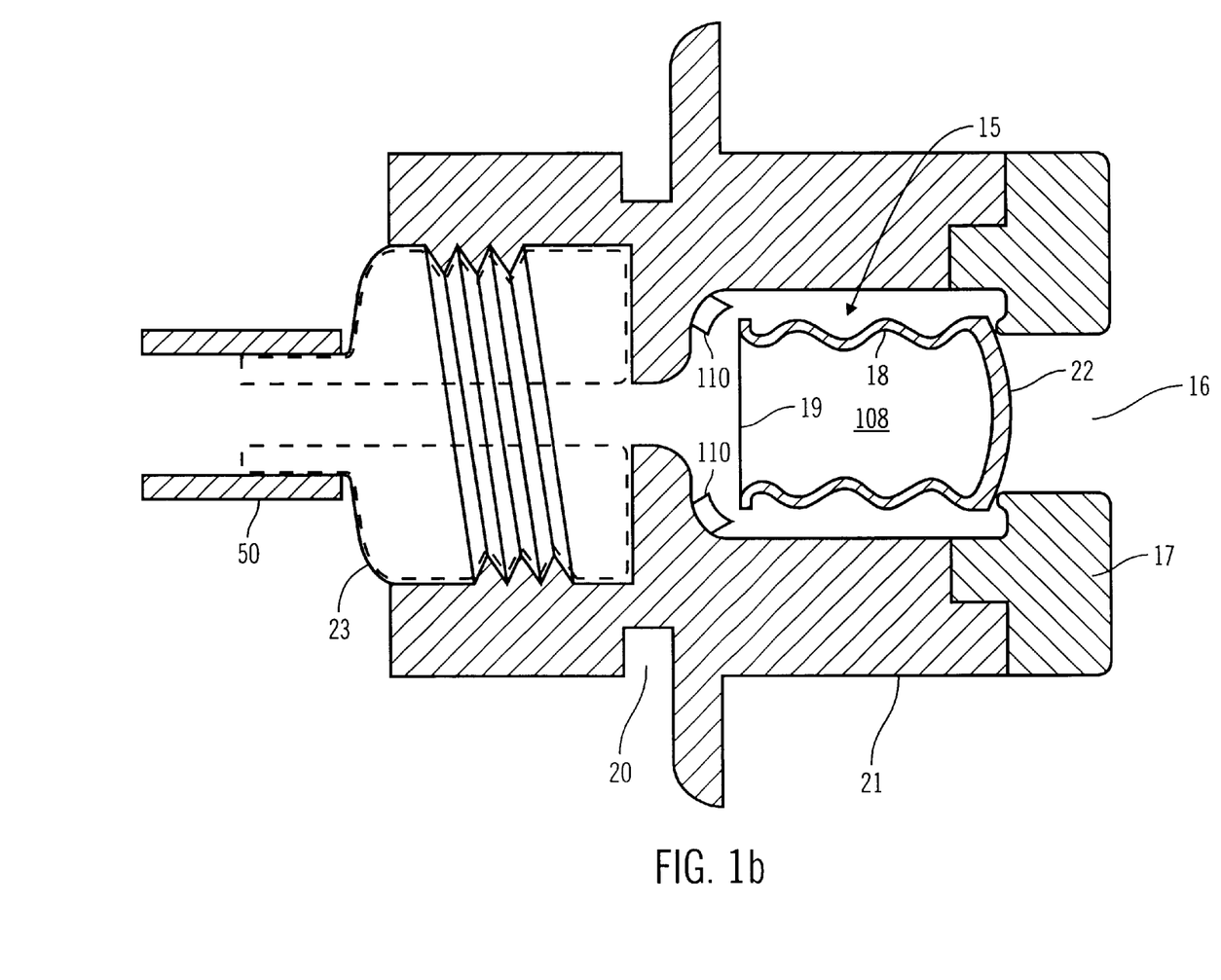
Figure 2:
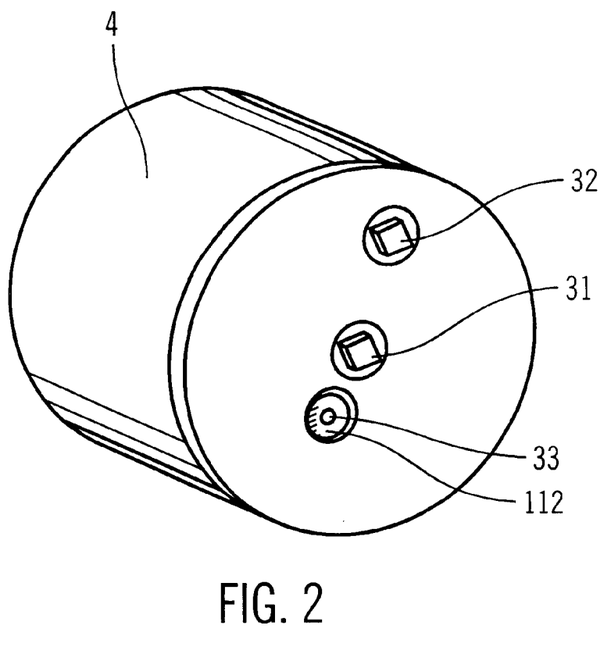
FIG. 2 is an end isometric view of the disposable showing the contacts that connect to a current generator in an infusion device shown in FIG. 4.

FIGS. 1a–2 illustrate a disposable reservoir 102 in accordance with the first embodiment of the present invention. The disposable reservoir 102 includes a housing 2, a gas power source assembly 104, an elastomeric sack 11, a regulating valve assembly 15 and an outlet 16. Preferably, the housing 2 is in the form of a cylindrical tube. In alternative embodiments, different cross-sectional shapes may be used, such as square, oval, elliptical, triangular, polygonal, or the like. Preferably, the disposable reservoir 102 is formed from glass, although other materials, such as plastic, metal, composites, laminates, or the like, may be used. Preferably, the gas power source assembly 104 and the regulating valve assembly 15 are inserted into the ends of the housing 102 to close and seal the disposable reservoir 102. Particular embodiments may secure and seal the gas power source 3 and the regulating valve assembly 15 using pressure fits, friction, snaps, detentes, "O" rings, adhesives, combinations of the preceding, or the like. Generally, all parts of the medication infusion device 100 or the disposable reservoir 102 that are in contact with medication should be made of materials that are protein compatible (such as bromobutyl rubber, glass, metal or the like) and should preferably be coated with a protein compatible coating, such as that disclosed in U.S. patent application Ser. No. 09/042, 138 filed Mar. 13, 1998 (published as PCT application WO 98/19627) and entitled "Implantable Medication Infusion system with Protein Stabilized Coating", and U.S. patent application Ser. No. 09/324,783 filed Jun. 3, 1999 and entitled "Medication Device with Polymer Protein Stabilized Surface Coating", both of which are herein specifically incorporated by reference.

As discussed, the back end of the disposable reservoir 102 includes a gas power source assembly 104, such as an electrolysis cell assembly, that is inserted as a plug 3. In the illustrated embodiment, the gas power source assembly 104 includes an interior cavity portion, which contains a conducting fluid such as dilute saline, or the like, in pure water. In alternative embodiments, other fluids such as acids, bases, or the like, may be used, or solids (such as potassium hydroxide, sodium hydroxide, or the like) or gels (such as gelatin mixed with electrolytes, polyhydroxy ethyl methacrylate, or the like) may be used for the conducting fluid. When current is applied across the two electrodes 5 and 6, which protrude through the plug 3 from the interior cavity of the gas power assembly 104 to the exterior of the disposable reservoir 102, electrolysis occurs in the solution contained in the interior cavity, creating a mixture of hydrogen and oxygen. For a single use disposable reservoir having 2 or 3 ml fluid capacity, the amount of saline solution required is small, on the order of less than 1/1000 of the drug capacity, but some excess fluid should be available to assure conduction throughout use. Because it is important to keep the electrodes 5 and 6 wet and conducting, some moistened sponge material or wicking material 8 can be used to maintain electrical contact between the electrolysis fluid and the electrodes 5 and 6. In alternative embodiments, the electrodes 5 and 6 may be large and close together so that the conducting path is small, and the hollow area of the plug can also be very small. In alternative embodiments, a flexible and/or gas permeable membrane 10 may provide sufficient pressure to compress and maintain the electrolysis fluid against the electrodes 5 and 6 as the liquid is slowly electrolyzed, and the sponge or wicking material may be omitted. When the gas is generated in the interior cavity, it diffuses through the membrane 10. Preferably, the membrane 10 is retained by a ring 9, or another part, of the gas power source assembly 104.

Attached to the interior side of the gas power source assembly 104 is an elastomeric sack 11 made of a drug compatible material such as bromobutyl rubber. In alternative embodiments, other flexible materials could be utilized. At the closed end of the sack 11 is a stiffening disk 12, to cause the elastomeric sack 11 to expand more uniformly. Alternatively, the elastomeric sack 11 may be a flexible elongated tube, which when empty is compressed when the disposable reservoir 102 is full. The elastomeric sack 11 expands as gas is generated by the gas power source to press against the sides of the housing 2 to expel medication (contained in the medication reservoir 4) through the outlet 16. In an alternative embodiment, the elastomeric sack 11 and stiffening disk 12 can be replaced with a syringe type plunger (without handle), with "O" rings or other seals to block leakage around the plunger, medication cartridge with a piston or the like. However, the use of these versions would be dependent on sufficiently low stiction between the plunger (or piston) and the syringe body (or medication cartridge) to avoid irregular and inconsistent infusion of the medication through the outlet 16.

A potential problem with conventional gas powered devices can occur due to changes in the ambient air pressure, since this can affect the flow rate of medication from the disposable reservoir. For instance, if the ambient pressure changes, the gas volume generated by a given electrolysis current will be inversely proportional to the absolute pressure, such that the rate of drug flow for a given current would be changed and result in the delivery of the medication at different rates. In another example of conventional systems, when the elastomeric sack 11 already contains a considerable gas volume (i.e., when the disposable reservoir is not fill), a sudden change in pressure, such as going up or down in an airplane, vehicle, or the like, can interrupt delivery or, even worse, can create a sudden bolus, which for some drugs could be dangerous. With a sudden decrease in ambient pressure, the gas volume will expand and cause an unprogrammed amount of drug to be delivered. With a sudden increase in ambient pressure, the gas volume in the gas power source 3 would be compressed, stopping delivery and causing body fluids to enter through an infusion set 50 (see FIG. 4*a*). However, these problems can be largely eliminated or substantially reduced by using the pressure regulating valve assembly 15 at the outlet 16.

The regulating valve assembly 15 illustrated in FIGS. 1*a* and 1*b* includes a chamber filled with a pressurized gas at a "reference" pressure slightly higher than standard atmospheric pressure. For instance, the "reference" pressure inside the reference pressure chamber 108 is preferably set slightly above atmospheric pressure, such as at 1.1 atmospheres. However, in alternative embodiments, higher (up to 2, 3, or more atmospheres) or slightly lower pressures (to 1.05 atmospheres) may be used. The reference pressure is an absolute pressure that adjusts due to changes in temperature and is a reference relative to the gas pressure generated by the gas power source 14. Thus, when the temperature of the gas in the gas power source 14 and the reference pressure chamber 108 are the same, the device will deliver fluid at the proper rate.

The reference pressure chamber 108 consists of a back plate 19, a chamber tube 18 (such as a bellows that can expand and contract longitudinally) and a valve sealing surface 22. The reference pressure chamber 108 is contained within the valve plate 17 and the valve body 21. Near the joint between the chamber tube 18 and the back plate 19 are gaps 110 around the chamber tube 18 for the medication to flow out through the regulating valve assembly 15, through the outlet 16 to the infusion set 50 (see FIG. 4*a*), which connects to the Luer fitting or other connection means 23 to the infusion set 50. The gas power source assembly 104 will generate sufficient gas in the gas chamber 105 to reach an internal pressure that is just above the reference pressure, which then compresses the chamber tube 18 toward the back plate 19, opening the valve sealing surface 22 and permitting flow around the chamber tube 18 to the outlet 16. No ambient pressure below the reference pressure will affect delivery, since the chamber tube 18 and the valve sealing surface 22 will not be displaced. The regulating valve assembly 15 will not protect against higher ambient pressures, so the reference pressure should be set at the highest level likely to be experienced under normal operating conditions. For unusual exposures, such as for swimming, the infusion device 100 could simply be removed so that any higher pressure is unlikely to be encountered. A one-way valve could also be incorporated to prevent back flow at high pressures. However, since the infusion device can be removed before these unusual exposures, a one-way valve may be omitted. Not incorporating a one-way valve is an advantage since a slightly higher filling pressure than the reference pressure will enable filling the disposable reservoir 102 through the outlet.

Figure 9:
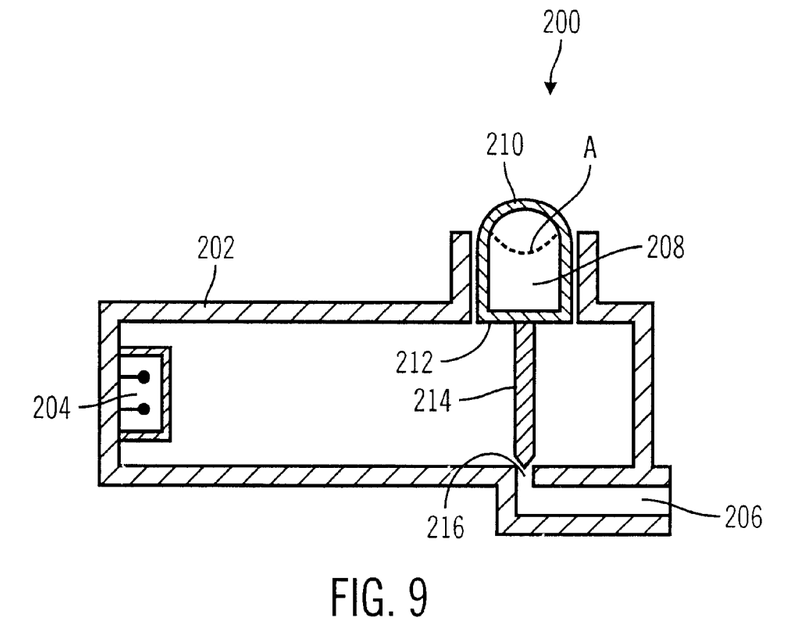
FIG. 9 is a cross-sectional view of a regulating valve assembly in accordance with another embodiment.

FIG. 9 shows a cross-section of a regulating valve assembly 200 in accordance with another embodiment of the present invention. The regulating valve assembly 200 is included in a reservoir housing 202 that holds a gas power source 204 and has an outlet 206 for fluid to be provided to a patient. The regulating valve assembly 200 includes a reference gas cell 208 with a top protrusion 210 and a bottom diaphragm 212. The bottom diaphragm 212 is connected to a needle valve 214 to control the flow of fluid through an opening 216 leading to the outlet 206. The top protrusion 210 is capable of being depressed (such as to the position A shown in dotted lines in FIG. 9) to set the reference gas pressure, as described above. Generally, the top protrusion 210 is depressed just prior to use, such as upon insertion of the reservoir housing 202 into an infusion device. This allows the reference gas cell 208 to be made from polymeric materials, such as rubber, plastic or the like. Thus, the reference gas cell does not require a metallic surface to prevent gas escaping during storage, since polymeric materials often allow gas to diffuse out of the gas cell over time. This would tend to reduce the cost of manufacturing the gas reference cell, since less expensive materials and manufacturing techniques could be used. The selected reference gas pressure is set by selecting a volume of the reference gas cell 208 and determining how much the volume will be decreased by compression of the top protrusion portion 210. Any suitable pressure can be selected by the choice of the relative volume sizes.

Figure 10:
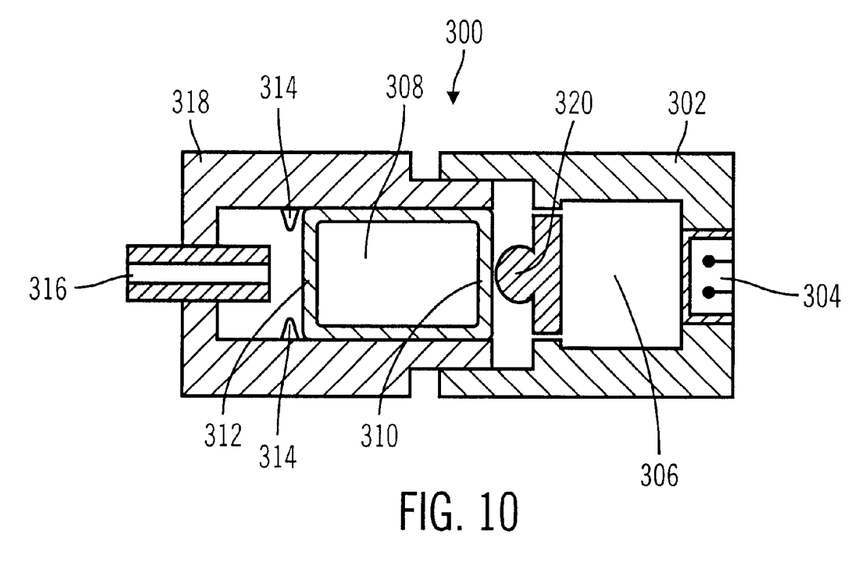
FIG. 10 is a cross-sectional view of a regulating valve assembly in accordance with a further embodiment.

FIG. 10 shows a cross-section of a regulating valve assembly 300 in accordance with another embodiment of the present invention. The regulating valve assembly 300 is included in a reservoir housing 302 that holds a gas power source 304 and has a fluid compartment 306 for fluid to be provided to a patient. The regulating valve assembly 300 includes a reference gas cell 308 with a compression wall 310 and a diaphragm 312. The diaphragm 312 contacts valve members 314 to control the flow of fluid through an opening to an outlet 316. The regulating valve assembly 300 is secured to the reservoir housing 302 by a slidable cap 318 that includes the valve members 314 and the outlet 316. The reservoir housing 302 also includes a compression member 320 for compressing the compression wall 310 to reduce the volume of the reference gas cell 308 when the slidable cap 318 is slid back against the reservoir housing 302. Preferably, the slidable cap 318 locks in position with a snap fit. However, alternative embodiments may utilize adhesives, threaded parts, or the like. The compression wall 310 is capable of being compressed to set the reference gas pressure, as described above. Generally, as in the embodiments shown in FIG. 9, the compression wall 310 is compressed just prior to use. This allows the reference gas cell 308 to be made from polymeric materials, such as rubber, plastic or the like. The selected reference gas pressure is set by selecting a volume of the reference gas cell 308 and determining how much the volume will be decreased by compression of the compression wall 310. Any suitable pressure can be selected by the choice of the relative volume sizes. This embodiment also provides an ability to fill the fluid compartment 306 through the outlet 316 prior to use, since the reference gas cell 308 is not engaged in a flow restricting configuration with the valve members 314 prior to sliding the slidable cap 318 against the reservoir housing 302. This permits filling through the outlet at the site of use, rather than prefilling at the site of manufacture.

Figure 3:
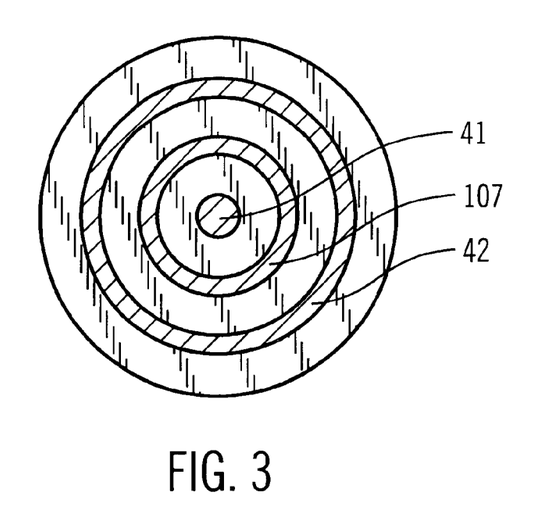
FIG. 3 is an end view of the electrical contacts on the inside of the infusion pump that is utilized to connect with the electrical contacts on the disposable reservoir.

FIG. 2 shows the rear of the disposable reservoir 102 illustrating the electrical contacts 31 and 32. In preferred embodiments, the electrical contacts 31 and 32 have "spring" contacts that upon insertion of the disposable reservoir 102 into the infusion device 100 make contact with the contact electrodes 41 and 42 on the inside rear of the reservoir chamber 40 of the infusion device 100 housing as shown in FIG. 3. The spring contacts 31 and 32, which are more fragile, are applied at the rear of the disposable reservoir 102, since they are replaced with each use and unlikely to wear out. Alternatively, if the spring contacts can be made sufficiently robust, the spring contacts may be placed on the infusion device 100 instead of and/or in addition to the spring contacts 31 and 32 on the disposable reservoir 102. Since the disposable reservoir 102 in this embodiment is round, the electrical contacts on the infusion device 100 should formed as rings 42 and 107 to assure proper electrical contact with the contacts 31 and 32 on the disposable reservoir.

FIGS. 1 and 2 also show a hole 112 with a pressure sensor 33. The pressure sensor 33 detects when the pressure in the disposable cartridge 102 rises materially above the "reference" pressure in the reference pressure chamber 108, indicating an occlusion of the outlet or catheter. There are a variety of ways such a pressure sensor can function. In this case a rubber or other elastomeric membrane 33 is stretched across the hole 112 in the plug 3. In this arrangement this membrane 33 is made conductive and contacts with electrode 31, one of the two electrical contacts on the disposable reservoir 102. When the pressure increases sufficiently to cause an occlusion alarm, the membrane 33 protrudes and makes contact with a ring electrode 107, which closes an alarm circuit in the infusion device 100, the other pole being the center electrode 31 of the gas power source assembly 104. As a safety feature, the pressure sensor can also turn off the electrolysis current to stop gas generation and avoid the possibility of high pressures. Other pressure sensor devices may be used. Also, other pressure sensors on the infusion device 100 may be used to measure ambient pressure and to adjust the gas generation rate to alter the internal pressure of the disposable reservoir 102 so that medication delivery is more precisely controlled.

Figure 5A:
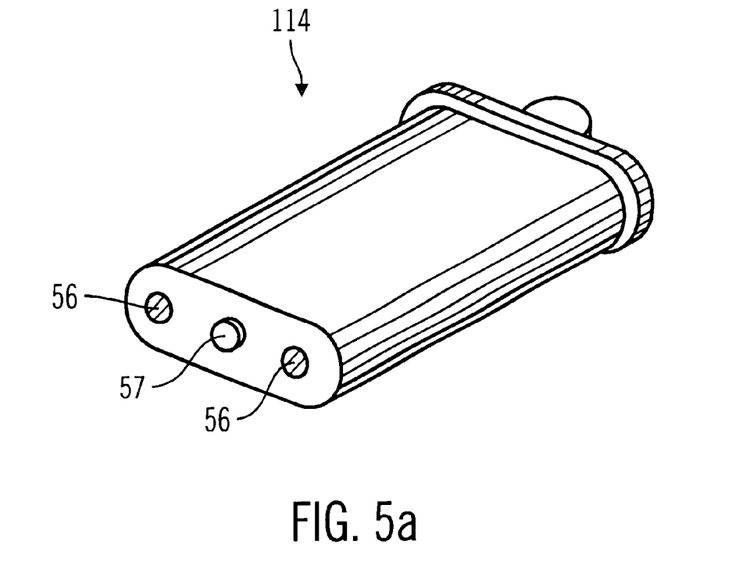
FIG. 5a is and isometric view of a disposable reservoir in accordance with a second embodiment of the present invention.
Figure 5B:
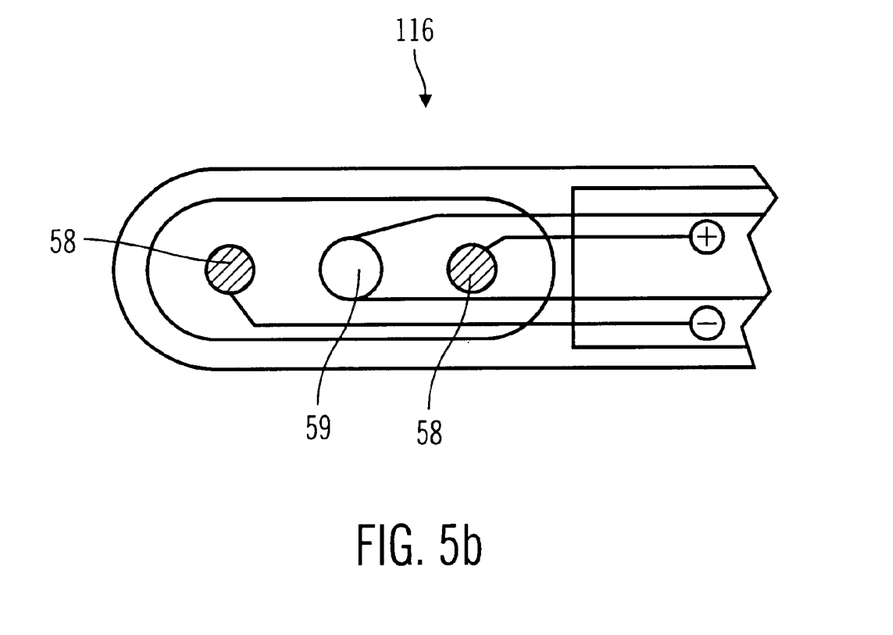

The first embodiment utilizes a round disposable reservoir 102. However, there is no need for the disposable reservoir to be round. FIG. 5a shows a disposable reservoir 114 with an oval cross-section. Although such a reservoir would not use standard round tubing and would call for a different sealing system at the opening into the infusion device 116 to inhibit water penetration, the thickness of the infusion device 116 would be reduced and the electrical contacts 56 formed on the disposable reservoir 114 to the infusion device 116 would be simpler, since the electrodes 56 would always be in a suitable orientation (i.e. one way or reversed 180° (the reversal would make no difference since polarity is not important)). A pressure sensor 57 would generally be located in the center. FIG. 5b illustrates the corresponding electrical contacts inside the infusion device 116. Here the+and−contacts 58 are located symmetrically to the sides and the pressure sensor contact 59 is in the center.

Figure 4A:
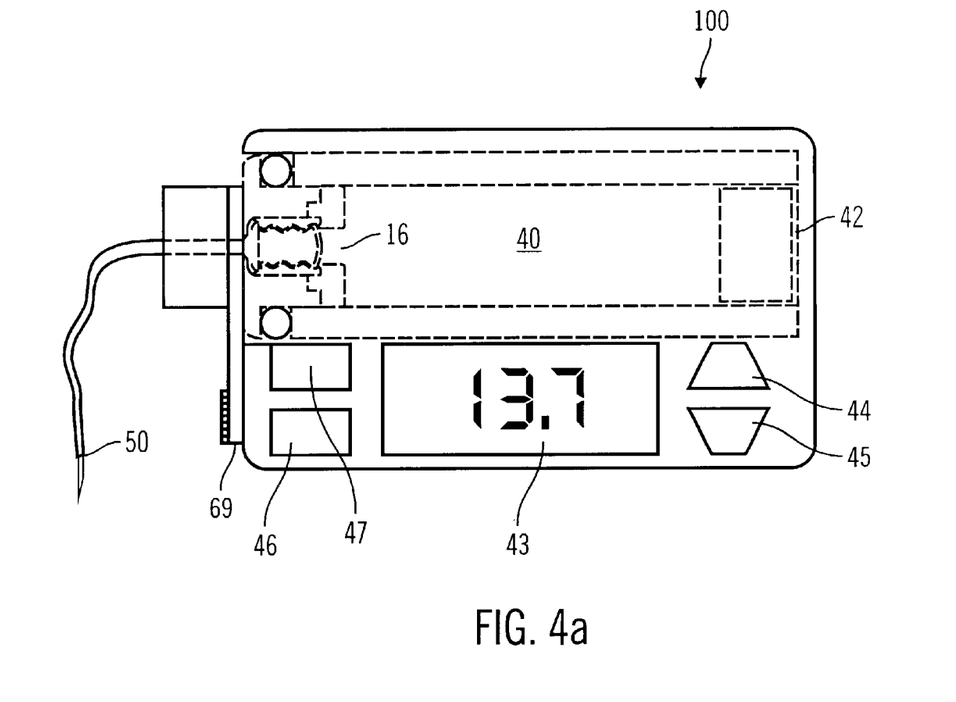
Figure 4B:
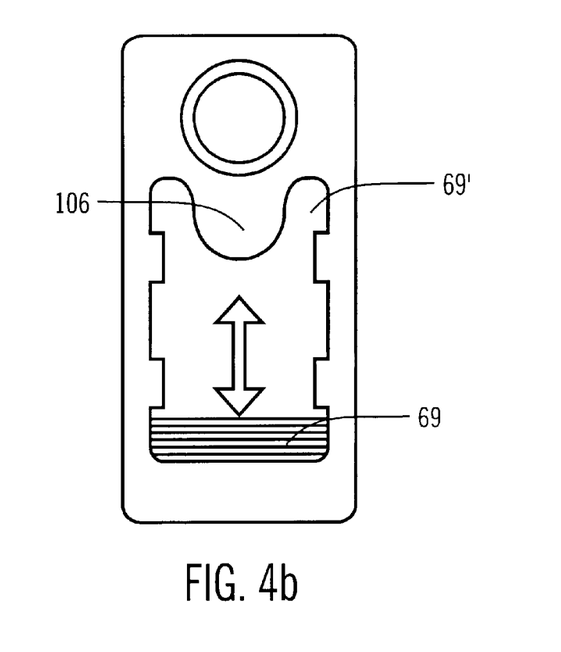
Figure 6:
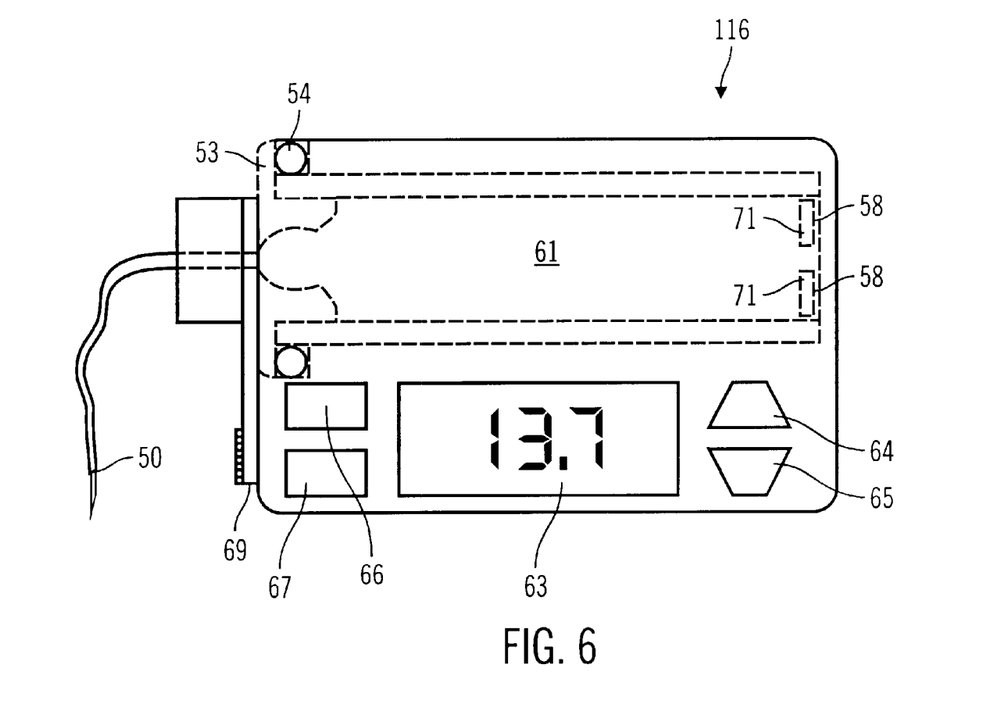

FIG. 6 illustrates an infusion device 116 incorporating the oval disposable reservoir 114 shown in FIG. 5a. The primary difference between the embodiments of FIGS. 4 and 6, other than details described above, is in the method of retaining the cartridge in the infusion device. In the embodiment of FIG. 6, a lip 53 of the valve regulating assembly is larger than the oval tube forming the disposable reservoir 114 so that it protrudes outside the tube. The surface of this lip 53 can retain a flat sealing gasket (or an "O" ring) 54 to seal against the housing of the infusion device 116. In use, the disposable reservoir would simply be inserted into the infusion device 116, compressing the gasket 54 and making electrical contact between electrodes 56 to their respective counterparts 58 on the infusion device 116. The slide retainer 69 or other retaining device on the pump is then pushed to lock the disposable reservoir 114 in the infusion device 116, forming a seal to maintain a moisture barrier to the inside of the disposable reservoir chamber of the infusion device 116. Since the moisture protection in the disposable reservoir chamber is not likely to be truly waterproof, the disposable reservoir chamber in the infusion device 116 that holds the disposable reservoir 114 should be separate from the section containing the display, control circuits, battery and the programming keys.

Figure 7A:
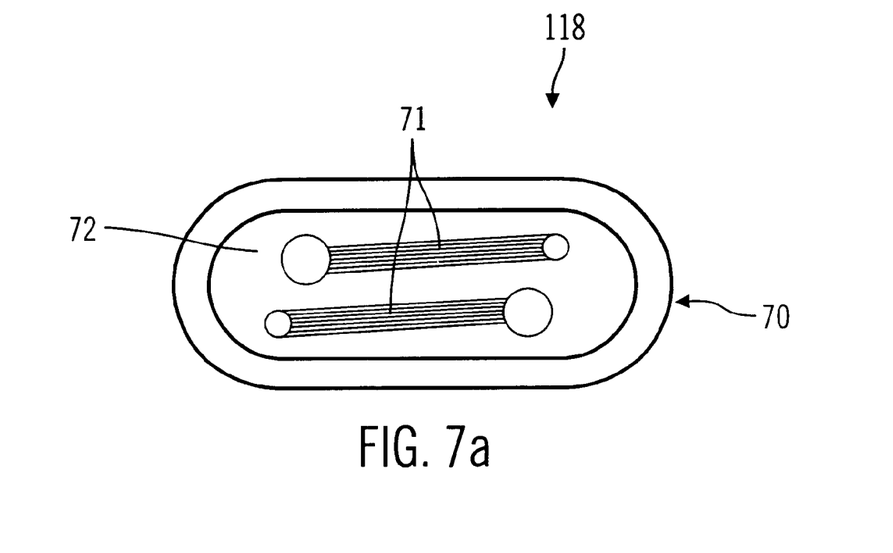
FIG. 7a shows an end view of the electrodes in the disposable reservoir shown in FIG. 5a that are used to generate the gas.
Figure 7B:
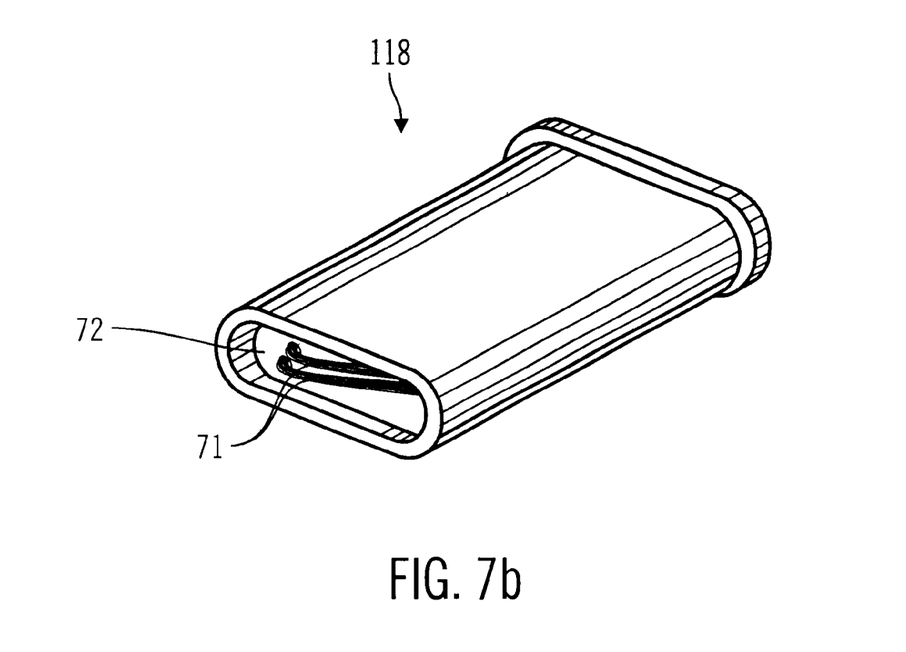

FIGS. 7a and 7b show a method of promoting electrolysis using electrodes that are formed as long wires 71 on the inside of a gas power source 118. The wires 71 protrude to the rear at the contacts and are staked at the far end. These electrodes are then buried in a wicking foam moisture cell 72. The long wires are more likely to be in contact with the electrically conducting fluid absorbed into the sponge. In alternative embodiments, the casing of the electrolysis cell (or gas power source) may be used as a ground terminal; obviating the need for two electrodes.

Figure 8A:
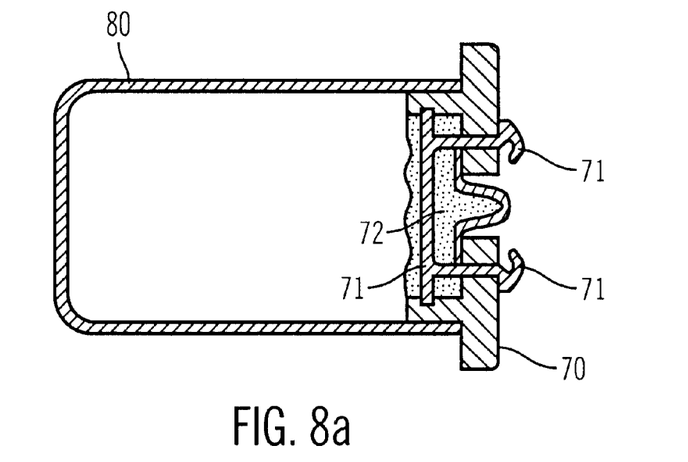
FIG. 8a shows a top cross-sectional view of a disposable reservoir in accordance with a third embodiment of the present invention.
Figure 8B:
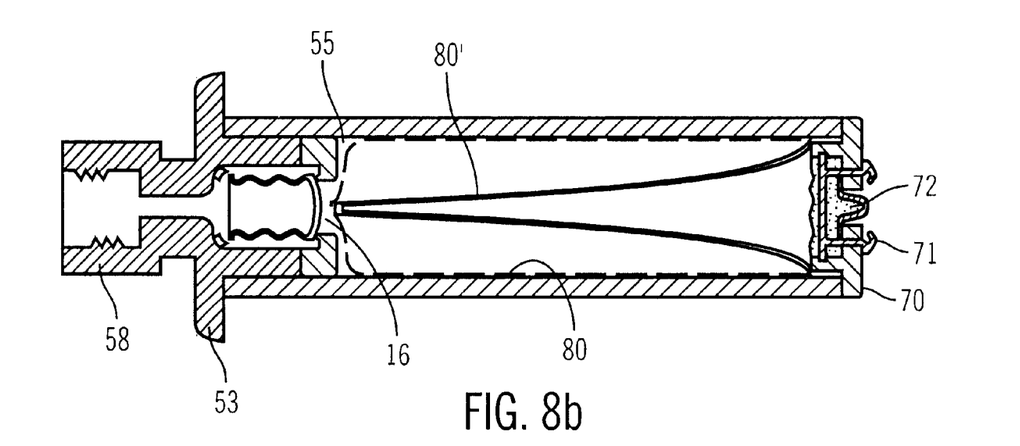

FIGS. 8a and 8b illustrates a sack 80 made of thin film so that when essentially empty the sides roll up or down as shown at 80 and 80'. When full of gas, the sack 80 will fill up, from the empty state of 80', and will fill virtually the entire inside of the cartridge 55, forcing essentially all the medication from the reservoir through the outlet 16, as shown in the dotted lines 80. This would replace the design shown in FIG. 1a.

Additional alternative embodiments may separate the gas power source and the medication reservoir into separate components. This would be beneficial when the gas power source is capable of being used for longer periods of time than the amount time needed to deliver the medication in the medication reservoir. For instance, the gas power source may be loaded into the device for two or more uses, and a replacement medication reservoir is engaged with the gas power source each time a new medication supply is required. When the gas power source is depleted a new gas power source is inserted into the device. In alternative embodiments, the gas power source is permanently mounted into the device and refilled with electrolytes and other necessary materials as required.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An external infusion device system for infusing a fluid into a patient, the system comprising:
   a reusable infusion device housing;
   a gas power source for generating a gas to expel the fluid from a fluid reservoir; and
   a disposable reservoir that is insertable into the reusable infusion device housing to infuse the fluid into the patient, wherein the disposable reservoir includes:
   a reservoir housing;
   a fluid reservoir within the reservoir housing for containing the fluid to be infused into the patient;
   an outlet in the reservoir housing through which the fluid is expelled to be infused into the patient;
   an expansion chamber disposed between the gas power source and the fluid reservoir to receive the gas from the gas power source and to expand into a part of the space occupied by the fluid reservoir to expel the fluid from the fluid reservoir; and
   a regulating valve assembly disposed between the fluid reservoir and the outlet to set a predetermined threshold pressure that must be exceeded to permit fluid to be expelled from the fluid reservoir through the outlet.

2. The system according to claim 1, wherein the gas power source utilizes electrolysis to generate the gas.

3. The system according to claim 1, further including a pressure sensor coupled to the gas power source to determine an excessive pressure in the expansion chamber to detect an occlusion.

4. The system according to claim 3, wherein the gas power source utilizes electrolysis to generate the gas, and wherein an electrolysis current is turned off when excessive pressure is detected.

5. The system according to claim 1, wherein gas power source includes a housing, and wherein the gas power source uses the housing of the gas power source as an electrode.

6. The system according to claim 1, wherein the disposable reservoir has a circular cross-section.

7. The system according to claim 1, wherein the disposable reservoir has an oval cross-section.

8. The system according to claim 1, wherein the expansion chamber is formed as a sack.

9. The system according to claim 1, wherein the regulating valve assembly is compressed prior to use to set the predetermined threshold pressure.

10. The system according to claim 1, wherein the regulating valve assembly sets the predetermined threshold pressure at greater than 1.05 atmospheres.

11. An disposable reservoir for use with an external infusion device system for infusing a fluid into a patient, the system comprising:
    a reservoir housing;
    a fluid reservoir within the reservoir housing for containing the fluid to be infused into the patient;
    an outlet in the reservoir housing through which the fluid is expelled to be infused into the patient;
    a gas power source contained within the reservoir housing for generating a gas to expel the fluid from the fluid reservoir;
    an expansion chamber in the form of an elastomeric sack disposed between the gas power source and the fluid reservoir to receive the gas from the gas power source and to expand into the fluid reservoir to expel the fluid from the fluid reservoir; and
    a regulating valve assembly disposed between the fluid reservoir and the outlet to set a predetermined threshold pressure that must be exceeded to permit fluid to be expelled from the fluid reservoir through the outlet.

12. The disposable reservoir according to claim 11, wherein the gas power source utilizes electrolysis to generate the gas.

13. The disposable reservoir according to claim 11, further including a pressure sensor coupled to the gas power source to determine an excessive pressure in the expansion chamber to detect an occlusion.

14. The disposable reservoir according to claim 11, wherein the gas power source utilizes electrolysis to generate the gas, and wherein an electrolysis current is turned off when excessive pressure is detected.

15. The disposable reservoir according to claim 11, wherein gas power source includes a housing, and wherein the gas power source uses the housing of the gas power source as an electrode.

16. The disposable reservoir according to claim 11, wherein the disposable reservoir has a circular cross-section.

17. The disposable reservoir according to claim 11, wherein the disposable reservoir has an oval cross-section.

18. The disposable reservoir according to claim 11, wherein the disposable reservoir has a rectangular cross-section.

19. The disposable reservoir according to claim 11, wherein the disposable reservoir has a triangular cross-section.

20. The disposable reservoir according to claim 11, wherein the expansion chamber is formed as a sack.

21. The disposable reservoir according to claim 20, wherein the regulating valve assembly is compressed prior to use to set the predetermined threshold pressure.

22. The disposable reservoir according to claim 11, wherein the regulating valve assembly sets the predetermined threshold pressure at greater than 1.05 atmospheres.

* * * * *